United States Patent [19]

Rosenberg

[11] Patent Number: 5,490,514
[45] Date of Patent: Feb. 13, 1996

[54] MEDICAL MANOMETER WITH FLEXIBLE FLUID COLLECTION TUBE

[76] Inventor: Norman M. Rosenberg, 11122 Alford, Brighton, Mich. 48116

[21] Appl. No.: 333,817

[22] Filed: Nov. 3, 1994

[51] Int. Cl.⁶ .................................................. A61B 5/00
[52] U.S. Cl. ............................ 428/674; 128/736; 73/748
[58] Field of Search ................................... 128/673, 674, 128/675, 736; 73/748

[56] References Cited

U.S. PATENT DOCUMENTS

| | | | |
|---|---|---|---|
| 3,435,819 | 4/1969 | Reynolds et al. | 128/674 |
| 3,561,431 | 2/1971 | Pannier, Jr. | 128/205 |
| 3,636,942 | 1/1972 | Nye | 128/674 |
| 3,730,168 | 5/1973 | McWhorter | 128/674 |
| 3,874,369 | 4/1975 | Pannier, Jr. | 128/674 |
| 3,980,082 | 9/1976 | Miller | 128/674 |
| 4,282,881 | 8/1981 | Todd et al. | 128/674 |
| 4,639,251 | 1/1987 | Kirkland | 604/260 |

FOREIGN PATENT DOCUMENTS 2075683  11/1981  United Kingdom ................... 128/674

OTHER PUBLICATIONS

*Medical Device Register*, vol. 1, 1993, Medical Economics Data, Montvale, NJ.

Primary Examiner—Angela D. Sykes
Assistant Examiner—Robert L. Nasser, Jr.
Attorney, Agent, or Firm—Gifford, Krass, Groh, Sprinkle, Patmore, Anderson & Citkowski

[57] ABSTRACT

A medical manometer replaces the conventional rigid vertical graduated cylinder with a flexible, graduated tube which is sufficiently pliable that it may be bent to drain the fluid collected during use. This flexibility further obviates the need for a stopcock or other type of valve, resulting in a device which is significantly lighter in weight and much more conducive to disposability. The improved manometer is specifically intended for use in measuring cerebro-spinal fluid pressure, in which case the device's simplicity and flexibility increase accuracy in positioning and minimize patient discomfort.

2 Claims, 2 Drawing Sheets

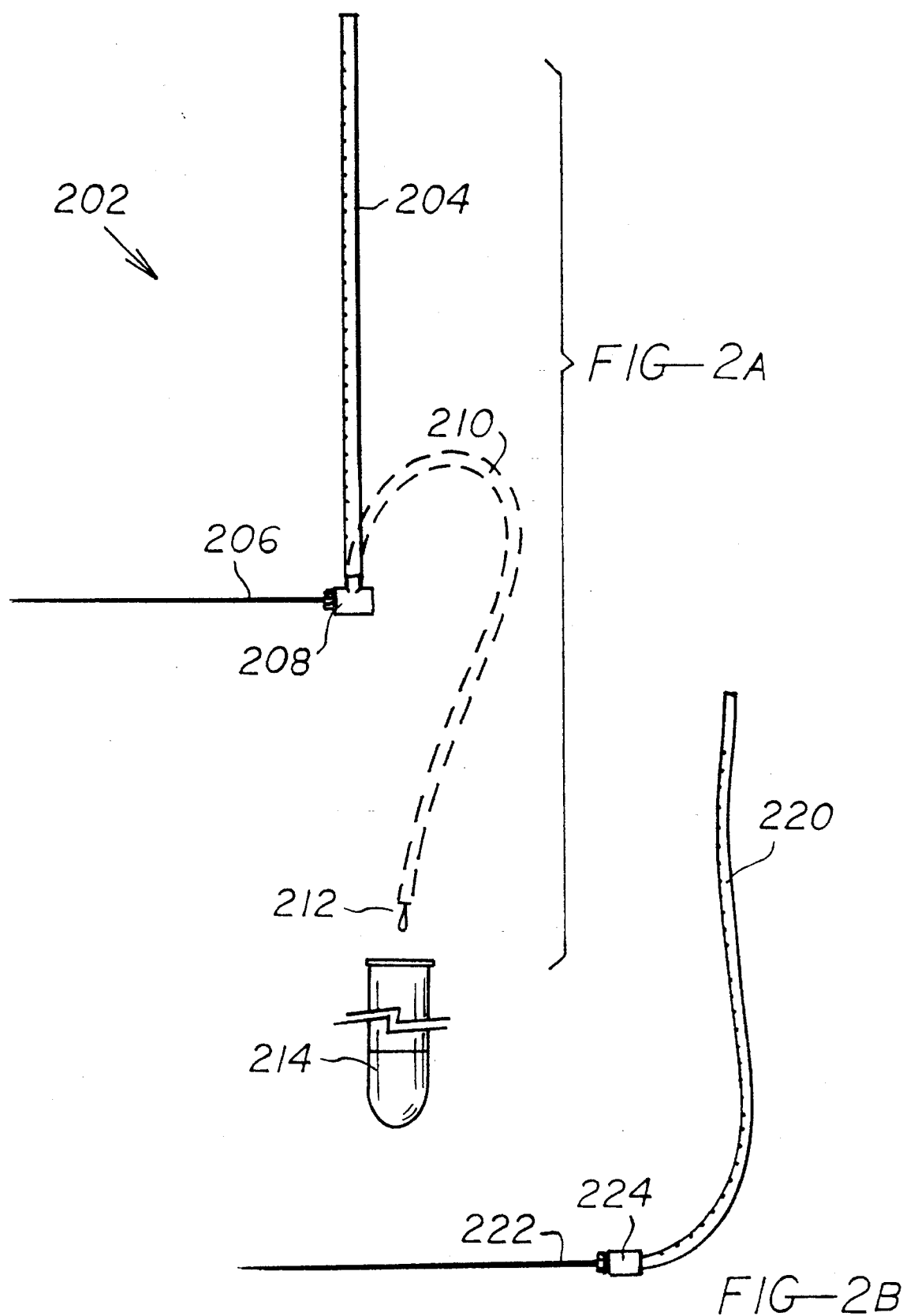

MEDICAL MANOMETER WITH FLEXIBLE FLUID COLLECTION TUBE

FIELD OF THE INVENTION

The present invention relates generally to medical manometers of the type used to measure the pressure of a bodily fluid such as cerebro-spinal fluid, and, more particularly, to such a manometer having a simplified fluid-carrying structure and a flexible graduated tube which may be bent to facilitate draining of the fluid collected.

BACKGROUND OF THE INVENTION

Existing manometers of the type for bodily fluid pressure measurement such as a spinal or lumbar manometers are large, rigid devices which may be awkward to use and intimidating, particularly to younger patients. Such devices typically include a stopcock body to which a lumbar penetrating needle is attached, the body further connecting to a rigid, elongated transparent cylinder with visual graduations. With the needle inserted into the lumbar intrathecal space, and with the cylinder oriented vertically and the stopcock adjusted so that fluid flows from the needle and enters into the cylinder, the physician compares the extent of the rise of the fluid to the gradations to obtain a pressure reading. As consecutive measurements may be necessary, for example, for beginning pressure and ending pressure, the stopcock is adjusted so that the fluid collected in the tube may drain out through the bottom of the body for collection so the procedure may be repeated.

Due to the elongated nature of the instrument, the position of the needle with respect to the length of the graduated tube, and the need to turn the stopcock, use of such a device is awkward, and may lead to the rupture of a blood vessel, resulting in an inaccurate reading or contamination. Additionally, especially with regard to younger patients, such an instrument may appear threatening, causing patient agitation, which may further increase the likelihood of mistakes in positioning or result in injury. Accordingly, any change in the construction of such an instrument which might lead to smoother operation and, hence, a more accurate reading or improve patient/physician rapport would be welcome by the profession.

SUMMARY OF THE INVENTION

The present invention is drawn toward a medical manometer employing a flexible, graduated tube having a first end connected in a fluid path to a cannulated needle and having an opened second end. The tube is oriented vertically during use with the opened, second end pointing upward to indicate fluid pressure by visually comparing the level of the fluid visible in the tube, which has gradations thereon. In the preferred embodiment, however, the tube is sufficiently flexible that it may be bent so as to point the opened, second end downward for the purpose of draining the fluid collected during use therefrom.

The flexibility of the graduated tube obviates the need for a stopcock or other type of valve, thus enabling the fluid path between the flexible, graduated tube and the needle to be non-valved and unobstructed. The pliable graduated tube is also preferably composed of a sufficiently soft material so that it may be easily cut to remove excess tubing material beyond the furthest extent of fluid collected during use.

Given the flexible tube, which is preferably small and less substantial than its rigid counterparts, and the lack of a valving mechanism, the inventive manometer is significantly lighter in weight and much more conducive to disposability. As such, the device may be curled for packaging and prior to use to ease patient apprehension and increase comfort and accuracy in positioning. The instrument is specifically intended for use in measuring cerebro-spinal fluid pressure within the an epidural cavity, though other uses, including cardio-vascular and urinary applications, may also benefit from the simplified design.

DESCRIPTION OF THE DRAWINGS

FIG. 2A is a side-view drawing of a spinal manometer constructed in accordance with the invention; and FIG. 2B is a side-view drawing of a spinal manometer constructed according to the invention wherein the fluid inlet portion to the graduated tube is coaxial with regard to the needle.

DETAILED DESCRIPTION OF THE PREFERRED EMBODIMENT

Figure 1:
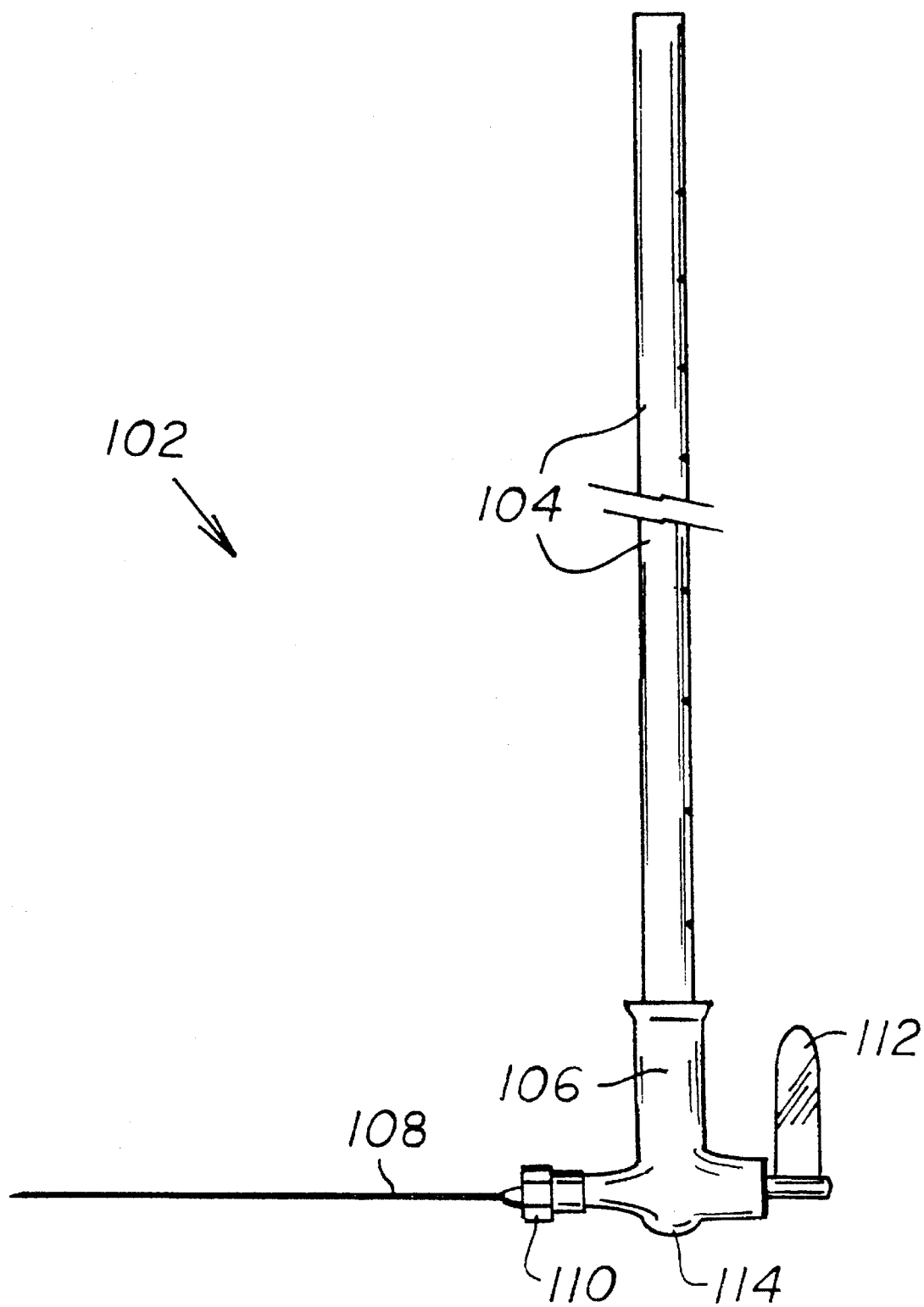
FIG. 1 is a side-view drawing of prior-art medical manometer of the type used to measure spinal fluid pressure.

In FIG. 1 there is drawn at 102 a side view of a prior art manometer of the type used to measure bodily fluid such as cerebro-spinal fluid. Graduated transparent cylinder 104, intended for vertical disposition during use, attaches to a connector body 106, which further attaches to a lumbar-puncturing needle 108 through a standard threaded fitting 110. A stopcock integrated into the connector body 108 includes a handle 112, which, in a first position, that being shown in the figure, allows fluid to travel into the cylinder 104 through the connector body 106. With the handle turned downwardly, however, the fluid, having been collected in tube 104, is allowed to flow out of the bottom of the connector body 106 through orifice 114 for collection and analysis.

This prior-art device works reliably in an ideal situation, however, due to the rigidity of the instrument, any movements made to the tube 104 or to the stopcock handle 112 or other components are transferred to the needle proper, causing it to move laterally, which may lead to inaccurate positioning and/or discomfort. Additionally, the appearance of the instrument is itself intimidating due to its large size and substantial physical make up.

The present invention improves upon this device, making it easier to use, more accurate and less threatening. Primarily, the invention replaces the standard rigid tube graduated cylinder with a flexible graduated tube, preferably smaller in diameter than in prior-art units and which is sufficiently pliable so that it may be emptied by simply pointing the open upper end downward and directly into a collection tube. As such, with the emptying being carried out by flexing the tube, the invention further eliminates the need for a stopcock of any kind, instead using a direct unimpeded and unobstructed fluid path from the needle into this flexible graduated tube. The graduated tube is preferably constructed of a transparent or at least translucent pliable plastic material.

FIG. 2A shows at 202 a preferred embodiment of the invention. The flexible tube 204 with graduations connects to a needle 206 through a hub or body 208. Preferably, the tube 204 is secured to the body 208 through a pressure-fit type of connection, and the body 208 further includes a threaded portion for attachment to a standardly provided lumbar-puncturing needle. Shown in broken-line form at 210 is the tube 204 having been flexed, such that the open end now points downwardly, enabling fluid previously connected to flow therefrom at 212 into a collection container 214 for subsequent analysis. In the event that fluid pressure is very low, resulting in little, if any fluid making its way into the tube, the tube may be disconnected from the hub to which the needle attaches, and the hub may be turned about the axis of the needle so as to drain fluid therefrom for collection.

Although the preferred embodiment depicted at 202 shows the use of a connection type of body 208, in fact, such a unit is optional in that the invention may be provided with the disposable needle being bonded directly and permanently to a disposable tube. Whether or not the body 208 is provided, however, the inventive device may be packaged and brought toward the patient with the tube 204 being curled, thereby significantly reducing the physical size of the device prior to and during use, thus reducing fear and agitation. Additionally, since the overall weight of this device is substantially reduced as compared to the prior art, and since the tube 204 is flexible, there should be far less undesirable movement of the needle 206 during insertion and use, thus significantly reducing problems associated with incorrect positioning.

Also in the preferred embodiment, the tube 204 is sufficiently soft that it may not only flex but may also be cut to a point just beyond the furthest extent of a fluid rise. For example, with a very high fluid pressure, the full extension of the tube may be necessary for reading in which case the entire tube may be bent over into the collection tube. However, if the reading is very low, resulting in the fluid only traveling a slight distance up the tube 204 during a measurement, the tube may be cut at a point just beyond this furthest extent of fluid travel so that it may be even more easily bent and/or rotated about the needle itself to facilitate drainage.

FIG. 2B shows an alternative embodiment wherein the tube 220 is coaxial with the needle, at least in the vicinity of their connection around the body 224. Again, this body 224 may either include threaded or pressure-fit connectors for the needle and graduated tube 220, respectively, or the needle may be bonded directly to the flexible tube 220 as shown, particularly if intended for disposability.

Having thus described my invention, I claim:

1. A method of measuring spinal fluid pressure comprising the steps of:

a) inserting a needle into a patient's epidural cavity, the needle being in fluid communication with a first end of a flexible, valveless tube, the flexible, valveless tube having a second end which is open to the air, the tube bearing graduation indicia along at least part of its length and having at least a portion of its circumference in the graduation-bearing region at least translucent, b) bending the tube so that a portion of the tube is in a vertical position with the open end pointing generally upward so that spinal fluid enters the tube and rises within it, c) reading the spinal pressure indication by visually comparing the level of fluid in the tube with the graduation indicia, and d) bending the tube to lower the open end of the tube so that the fluid drains out of the tube.

2. The method of claim 1 further comprising the step of cutting the tube to a desired length for ease of use.

* * * * *